(12) United States Patent
Den Boef

(10) Patent No.: US 9,909,996 B2
(45) Date of Patent: *Mar. 6, 2018

(54) DIFFRACTION BASED OVERLAY METROLOGY TOOL AND METHOD OF DIFFRACTION BASED OVERLAY METROLOGY

(71) Applicant: ASML Netherlands B.V., Veldhoven (NL)

(72) Inventor: Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,825

(22) Filed: Mar. 10, 2014

(65) Prior Publication Data

US 2014/0192338 A1 Jul. 10, 2014

Related U.S. Application Data

(63) Continuation of application No. 13/676,562, filed on Nov. 14, 2012, now Pat. No. 8,670,118, which is a
(Continued)

(51) Int. Cl.
G01N 21/956 (2006.01)
G03F 7/20 (2006.01)

(52) U.S. Cl.
CPC ..... G01N 21/95607 (2013.01); G03F 7/7015 (2013.01); G03F 7/70633 (2013.01)

(58) Field of Classification Search
CPC .. G03F 7/70633; G03F 7/7015; G03F 9/7088; G03F 9/70; G01N 21/95607; G01N 33/5011; G01N 33/6803
(Continued)

(56) References Cited

U.S. PATENT DOCUMENTS 4,332,473 A 6/1982 Ono
4,999,014 A 3/1991 Gold et al.
(Continued)

FOREIGN PATENT DOCUMENTS

CN 1916603 A 2/2007
EP 1 628 164 A2 2/2006
(Continued)

OTHER PUBLICATIONS

International Search Report directed to related International Patent Application No. PCT/NL2008/050785, mailed Mar. 25, 2009; 3 pages.
(Continued)

Primary Examiner — Tu Nguyen
(74) Attorney, Agent, or Firm — Sterne, Kessler, Goldstein & Fox P.L.L.C.

(57) ABSTRACT

Systems, methods, and apparatus are provided for determining overlay of a pattern on a substrate with a mask pattern defined in a resist layer on top of the pattern on the substrate. A first grating is provided under a second grating, each having substantially identical pitch to the other, together forming a composite grating. A first illumination beam is provided under an angle of incidence along a first horizontal direction. The intensity of a diffracted beam from the composite grating is measured. A second illumination beam is provided under the angle of incidence along a second horizontal direction. The second horizontal direction is opposite to the first horizontal direction. The intensity of the diffracted beam from the composite grating is measured. The difference between the diffracted beam from the first illumination beam and the diffracted beam from the second illumination beam, linearly scaled, results in the overlay error.

19 Claims, 5 Drawing Sheets

Related U.S. Application Data continuation of application No. 12/747,795, filed as application No. PCT/NL2008/050785 on Dec. 9, 2008, now Pat. No. 8,339,595.

(60) Provisional application No. 61/006,073, filed on Dec. 17, 2007.

(58) Field of Classification Search
USPC .................................................. 356/237.5
See application file for complete search history.

(56) References Cited

U.S. PATENT DOCUMENTS

| | | | |
|---|---|---|---|
| 5,689,339 A * | 11/1997 | Ota et al. .................... 356/401 |
| 6,153,886 A * | 11/2000 | Hagiwara et al. ............ 250/548 |
| 6,317,211 B1 | 11/2001 | Ausschnitt et al. |
| 6,458,605 B1 | 10/2002 | Stirton |
| 7,009,704 B1 | 3/2006 | Nikoonahad et al. |
| 7,433,040 B2 | 10/2008 | Mieher et al. |
| 7,561,282 B1 | 7/2009 | Widmann |
| 7,564,554 B2 | 7/2009 | Weiss |
| 7,663,753 B2 | 2/2010 | Mieher et al. |
| 7,700,247 B2 | 4/2010 | Ausschnitt |
| 7,791,727 B2 | 9/2010 | Den Boef et al. |
| 7,933,016 B2 | 4/2011 | Mieher et al. |
| 8,339,595 B2 | 12/2012 | Den Boef |
| 8,670,118 B2 | 3/2014 | Den Boef |
| 8,834,144 B2 | 9/2014 | Kanamura et al. |
| 2001/0030299 A1 | 10/2001 | Shiraishi |
| 2002/0158193 A1* | 10/2002 | Sezginer et al. .......... 250/237 G |
| 2004/0137651 A1 | 7/2004 | Smedt et al. |
| 2005/0012928 A1 | 1/2005 | Sezginer et al. |
| 2006/0033921 A1 | 2/2006 | Den Boef et al. |
| 2006/0066855 A1 | 3/2006 | Boef et al. |
| 2006/0117293 A1 | 6/2006 | Smith et al. |
| 2006/0132807 A1 | 6/2006 | Abdulhalim et al. |
| 2007/0279630 A1 | 12/2007 | Kandel et al. |
| 2010/0328655 A1 | 12/2010 | Den Boef |
| 2013/0155406 A1 | 6/2013 | Den Boef |

FOREIGN PATENT DOCUMENTS

| | | |
|---|---|---|
| JP | 11-121351 A | 4/1999 |
| JP | 2006-060214 A | 3/2006 |
| JP | 2006-165371 A | 6/2006 |
| WO | WO 97/45773 A1 | 4/1997 |
| WO | WO 99/39376 A1 | 8/1999 |
| WO | WO 02/065545 A2 | 8/2002 |
| WO | WO 02/069390 A2 | 9/2002 |
| WO | WO 2009/078708 A1 | 6/2009 |

OTHER PUBLICATIONS

International Preliminary Report on Patentability and Written Opinion of the International Searching Authority directed to related International Patent Application No. PCT/NL2008/050785, issued Jun. 22, 2010; 9 pages.

Non-Final Rejection mailed Apr. 24, 2012 for U.S. Appl. No. 12/747,795, filed Aug. 16, 2010; 9 pages.

Notice of Allowance mailed Aug. 16, 2012 for U.S. Appl. No. 12/747,795, filed Aug. 16, 2010; 7 pages.

Non-Final Rejection mailed Apr. 15, 2013 for U.S. Appl. No. 13/676,562, filed Nov. 14, 2012; 8 pages.

Final Rejection mailed Aug. 2 2013 for U.S. Appl. No. 13/676,562, filed Nov. 14, 2012; 7 pages.

Notice of Allowance mailed Oct. 11, 2013 for U.S. Appl. No. 13/676,562, filed Nov. 14, 2012; 9 pages.

Korean Office Action (with English-lanuage translation) directed to related Korean Patent Application No. KR20167014359; mailed Jul. 13, 2016; 9 pages.

"Overlay and Grating Line Shape Metrology Using Optical Scatterometry: Final Report", DARPA Report, ADB176711, published Aug. 31, 1993, publically released Nov. 20, 2001; 40 pages.

* cited by examiner

DIFFRACTION BASED OVERLAY METROLOGY TOOL AND METHOD OF DIFFRACTION BASED OVERLAY METROLOGY

This patent application is related to U.S. application Ser. No. 13/676,562, U.S. application Ser. No. 12/747,795, International Application No. PCT/NL08/50785 and U.S. Provisional Patent Application 61/006,073, which are incorporated by reference herein in their entireties.

FIELD

The present invention relates to a diffraction based overlay metrology tool and method of diffraction based overlay metrology.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

For lithographic processing, the location of patterns in subsequent layers on the substrate should be as precise as possible for a correct definition of device features on the substrate, which features all should have sizes within specified tolerances. The overlay error (i.e., the mismatch between subsequent layers) should be within well-defined tolerances for creating functional devices.

To this end, an overlay measurement module is generally used for determining the overlay error of a pattern on the substrate with a mask pattern as defined in a resist layer on top of the pattern.

The overlay measurement module typically performs the measurement with optics. The position of the mask pattern in the resist layer relative to the position of the pattern on the substrate is determined by measuring an optical response from an optical marker which is illuminated by an optical source. The signal generated by the optical marker is measured by a sensor arrangement. Using the output of the sensors the overlay error can be derived. Typically, the patterns on which overlay error are measured are located within a scribe lane in between target portions.

Two basic concepts are known for overlay metrology.

A first concept relates to measurement of overlay error that is image based. A position of an image of the pattern on the substrate is compared to the position of the mask pattern in the resist layer. From the comparison the overlay error is determined. An example to measure overlay error is the so-called box-in-box structure, in which the position of an inner box within an outer box is measured relative to the position of the outer box.

Image based overlay error measurement may be sensitive to vibrations and also to the quality of focus during measurement. For that reason, image based overlay error measurement may be less accurate in environments that are subjected to vibrations, such as within a track system. Also, image-based overlay measurements may be susceptible to aberrations in the optics that may further reduce the accuracy of the measurement.

A second concept relates to measurement of overlay error that is diffraction based. In the pattern layer on the substrate a first grating is located, and in the resist layer a second grating is located with a pitch that is, substantially identical to the first grating. The second grating is located nominally on top of the first grating. By measuring the intensity of the diffraction pattern as generated by the first and second grating superimposed on each other, a measure for the overlay error may be obtained. If some overlay error is present between the first and second grating, this is detectable from the diffraction pattern.

In diffraction based overlay error measurement, only the first and second gratings may be illuminated, since light that reflects from adjacent regions around the gratings interferes with the intensity level of the diffraction pattern. However, a trend emerges to have overlay error measurements close to critical structures within a die (and not necessarily within the scribe lane). Also, there is a demand to reduce the size of gratings so as to have a larger area available for circuitry. To some extent, such demands can be accommodated by a reduction of the cross section of the illumination beam that impinges on the first and second gratings so as to avoid illumination of the region outside the gratings. However, the minimal cross-section of the illumination beam is fundamentally limited by the laws of physics (i.e. limitation due to diffraction). Below, the cross-sectional size in which diffraction of the beam occurs will be referred as the diffraction limit.

SUMMARY

It is desirable to have an improved diffraction based overlay error measurement system and method.

According to an aspect of the invention, there is provided a method for determining overlay error between a first pattern on a surface of a substrate and a second pattern superimposed on the first pattern, the substrate comprising a first grating in the first pattern and a second grating on top of the first grating, the second grating having substantially identical pitch as the first grating, the second and first gratings forming a first composite grating, the method including: providing a first illumination beam for illuminating at least the first composite grating under an angle of incidence along a first horizontal direction along the surface of the substrate, the substrate being in a fixed position, and measuring a first intensity of a first order diffracted beam from the first composite grating; and providing a second illumination beam for illuminating at least the first composite grating under the angle of incidence along a second horizontal direction along the surface of the substrate, wherein the second horizontal direction is opposite to the first horizontal direction, the substrate being in the fixed position, and measuring a second intensity of a negative first order diffracted beam from the first composite grating.

According to an aspect of the invention, the method further includes determining an intensity difference between the first intensity and the second intensity, the intensity difference being proportional to the overlay error between the first grating and the second grating.

According to an aspect of the invention, the first and second illumination beams are portions of a common illumination beam.

According to an aspect of the invention, the common illumination beam has an annular cross-section.

According to an aspect of the invention, the angle of incidence is oblique relative to the surface of the substrate, the diffraction angle of the first and negative first diffraction beam relative to the normal of the surface being smaller than the angle of incidence.

According to an aspect of the invention, the angle of incidence is substantially perpendicular to the surface of the substrate, and the method includes using the first illumination beam as the second illumination beam, and the measuring of the first intensity of the first order diffracted beam from the first composite grating and of the second intensity of the first order diffracted beam from the first composite grating being performed consecutively during provision of the first illumination beam.

According to an aspect of the invention, the method includes: blocking beams of diffraction order other than the first diffraction order when providing the first illumination beam; blocking beams of diffraction order other than the negative first diffraction order when providing the second illumination beam.

According to an aspect of the invention, the measuring of the first intensity of the first order diffracted beam from the composite grating includes: detecting an image of the composite grating obtained by only the first order diffracted beam by pattern recognition, and the measuring of the second intensity of the composite grating obtained by only the negative first order diffracted beam from the composite grating includes: detecting an image of the composite grating obtained by only the negative first order diffracted beam by pattern recognition.

According to an aspect of the invention, the method includes providing a second composite grating on the substrate, the second composite grating being formed by a third grating in the first pattern and a fourth grating on top of the first grating, the third grating and fourth having substantially identical pitch as the first and second grating, in which the first composite grating is biased with a first shift in a shift direction along the grating direction and the second composite grating is biased with a second shift in the shift direction along the grating direction, the first shift being different from the second shift; providing the first illumination beam for illuminating the second composite grating under an angle of incidence along the first horizontal direction along the surface of the substrate, the substrate being in the fixed position, and measuring a first intensity of a first order diffracted beam from the second composite grating; providing the second illumination beam for illuminating the second composite grating under the angle of incidence along the second horizontal direction along the surface of the substrate, and measuring a second intensity of a negative first order diffracted beam from the second composite grating.

According to an aspect of the invention, there is provided a detection system configured to determine overlay error between a first pattern on a surface of a substrate and a second pattern superimposed on the first pattern, including an illumination source, a plurality of lenses, an aperture stop and an image detector, the plurality of lenses being arranged along an optical path between a substrate position for holding a substrate and the image detector; the substrate including a first grating in the first pattern and a second grating on top of the first grating, the second grating having identical pitch as the first grating, the second and first gratings forming a composite grating; the illumination source being arranged to form a first illumination beam for illuminating the composite grating on the substrate under an angle of incidence along a first horizontal direction along the surface of the substrate, the substrate being in the substrate position; the image detector being arranged to receive a first order diffracted beam from the composite grating; the illumination source being arranged to form a second illumination beam for illuminating the composite grating on the substrate under an angle of incidence along a second horizontal direction along the surface of the substrate wherein the second horizontal direction is opposite to the first horizontal direction, the substrate being in the substrate position, the image detector being arranged to receive a negative first order diffracted beam from the composite grating.

According to an aspect of the invention, there is provided a lithographic apparatus including a detection system for determining overlay error between a first pattern on a surface of a substrate and a second pattern superimposed on the first pattern as described above.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
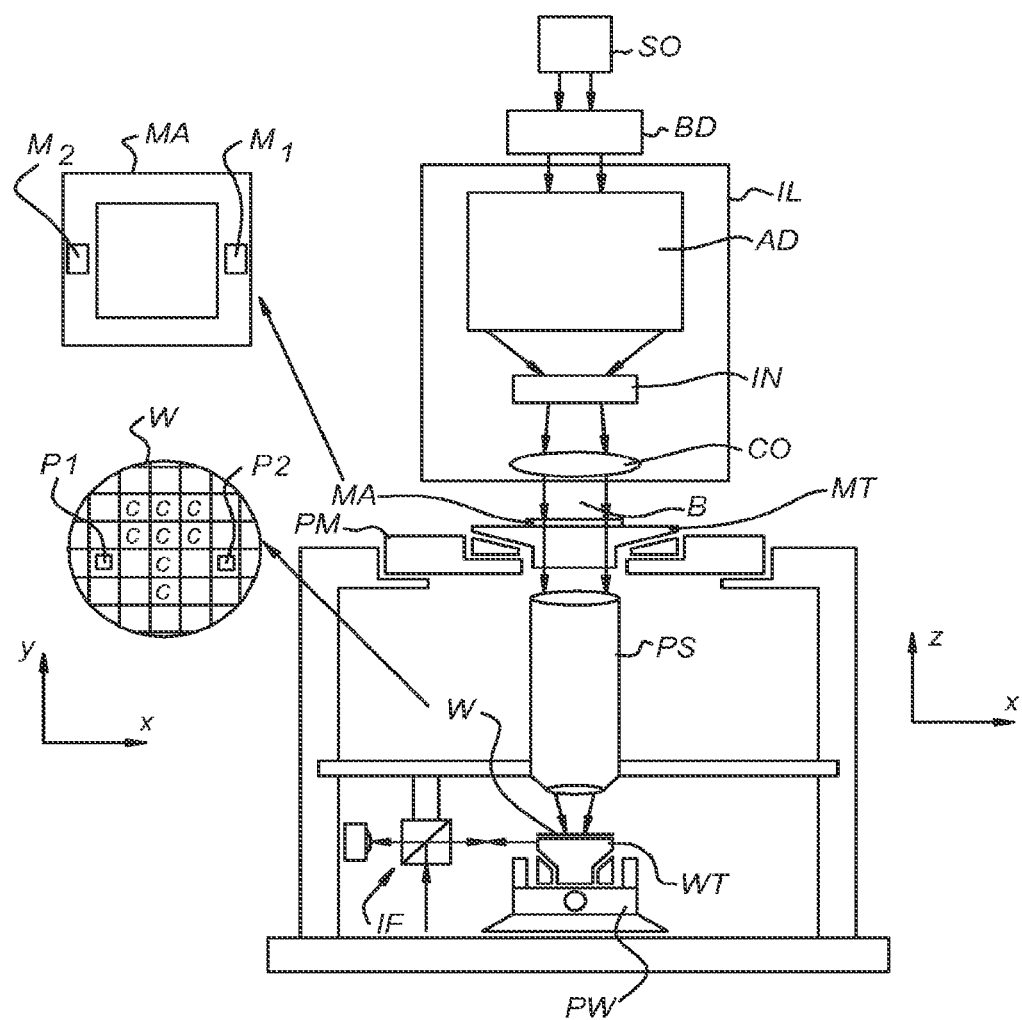
FIG. 1 depicts a lithographic apparatus according to an embodiment of the invention.

FIG. 1 schematically depicts a lithographic apparatus according to one embodiment of the invention. The apparatus includes an illumination system (illuminator) IL configured to condition a radiation beam B (e.g. UV radiation or EUV radiation); a patterning device support or a support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support or support structure holds the patterning device in a manner that depends on the orientation of the patterning device, the design of the lithographic apparatus, and other conditions, such as for example whether or not the patterning device is held in a vacuum environment. The patterning device support or support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device (e.g. mask) and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support or support structure (e.g., mask table MT), and is patterned by the patterning device. Having traversed the patterning device (e.g. mask) MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g. mask) MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2A:
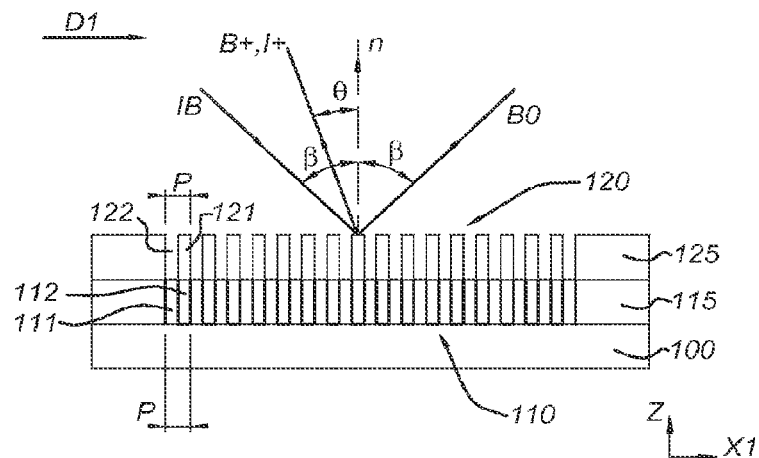
FIGS. 2a, 2b, 2c illustrate overlay error metrology based on diffraction according to an embodiment.
Figure 2B:
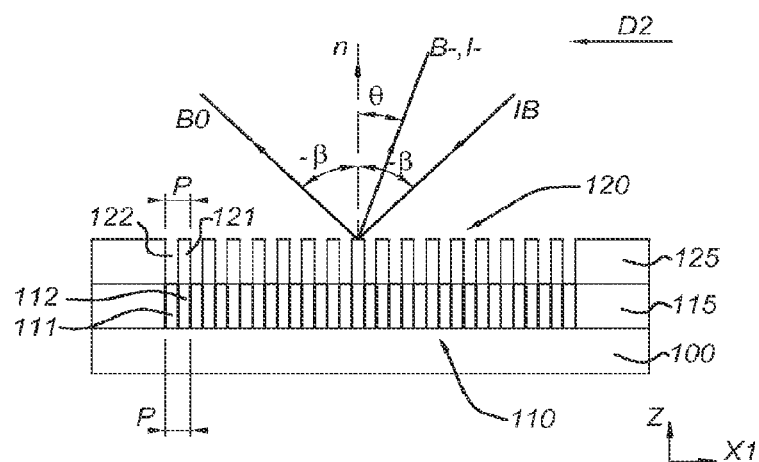
Figure 2C:
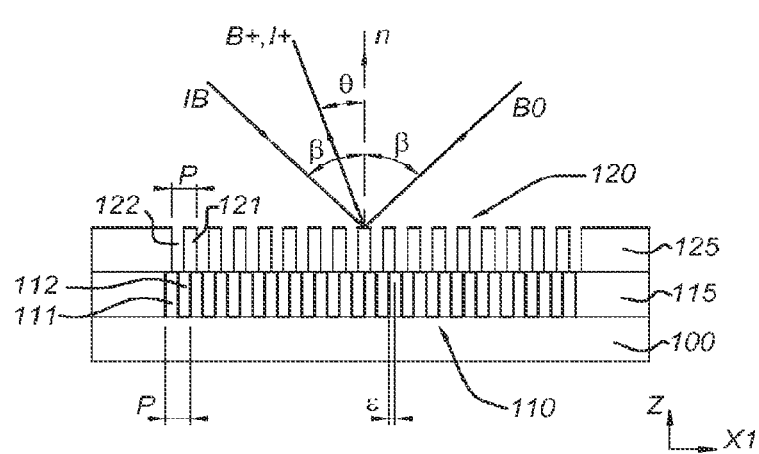

FIGS. 2a, 2b, 2c illustrate the interaction between an illumination beam and 2 overlapping gratings that may be used for diffractive overlay metrology according to an embodiment.

In FIG. 2a a cross section of a composite grating 110, 120 is shown which exhibits a zero overlay error.

On a substrate 100 a composite grating is constructed which includes of a first grating 110 and a second grating 120. The first grating 110 is patterned in the substrate material and includes a first periodic structure along a grating direction X1.

In an embodiment, the periodic structure of the first grating includes a plurality of primary lines 111 with secondary lines 112 interposed. The periodic structure is formed in layer 115.

For reason of clarity, only one primary line 111 and one adjacent secondary line 112 have been indicated by reference numbers in FIG. 2a.

The pitch P of the grating 110 is equal to the width of one line 111 and one secondary line 112.

As will be appreciated by the skilled in the art, the secondary lines 112 may be created from trenches in between the substrate lines 111 that are filled by a material different from the substrate material. For example, the substrate material is silicon and the trench material is a dielectric like silicon dioxide, or a metal like tungsten or copper.

On top of the first grating 110, a second grating 120 is present. The second grating consists of a second periodic structure.

In the embodiment shown, the second periodic structure includes plurality of lines 121 with trenches 122 interposed along the grating direction X1.

In this example, lines 121 are positioned on top of the secondary lines 112 of the first grating 110. The second grating 120 has a pitch P' in direction X1 equal to the width of one line 121 and one trench 122. The pitch P' of the second grating 120 is chosen to be substantially equal to the pitch P of the first grating 110. In an embodiment, lines 121 of the second grating 120 may have substantially the same width as the secondary lines 112 of the first grating 110.

Alternatively, lines 121 of the second grating 120 may be located on top of the primary lines 111 of the first grating 110.

The second grating may be a pattern formed in a resist layer 125.

In the case of FIG. 2a, the alignment of the first and second gratings 110 and 120 is perfect, the mismatch is ideally zero (which will be referred to as a zero overlay error). The lines 121 of the second grating 120 are aligned fully with the secondary lines 112 of the first grating 110.

In FIG. 2a, an embodiment for the interaction between an illumination beam IB and the composite grating 110, 120 is schematically shown.

In this embodiment, the illumination beam IB impinges under a first oblique incidence angle $\beta$ on the grating structure in grating direction X1. The angle of incidence $\beta$ is taken relative to the surface normal n. The illumination beam IB is scattered by the composite grating 110, 120 and forms (at least) two diffracted beams B+ and B0 of first order and zeroth order respectively, The first order diffracted beam B+ leaves the substrate under an angle $\theta$ (relative to the surface normal n) and the zeroth order diffracted beam leaves under specular reflection, respectively. It is noted that the pitch P of the composite grating 110, 120 and the wavelength of the illumination beam IB are chosen so as to fulfill the diffraction condition. In FIG. 2a, the diffraction orders and illumination beam are shown in one plane but this is just for convenience. An embodiment of the invention is also applicable in case of conical diffraction where the diffracted beams may not be in the same plane as the illumination beam.

Depending on the ratio of the grating's pitch P (with P=P') and the wavelength of the illumination beam IB also higher order diffracted beams may be present but these are ignored here.

In FIG. 2b, the same cross section of the composite grating 110, 120 of FIG. 2a for a second oblique incidence of the illumination beam IB.

In FIG. 2b, the illumination beam IB impinges under a second oblique incidence angle $-\beta$ on the grating structure. Second incidence angle $-\beta$ has substantially the same magnitude as the first incidence angle $\beta$, but is, in comparison, directed in an opposite direction along grating direction X1. The second angle of incidence $-\beta$ is taken relative to the surface normal n.

The illumination beam IB is scattered by the composite grating 110, 120 and forms (at least) two diffracted beams B− and B0 of first (negative) order and zeroth order respectively, which leave the substrate under an angle $-\theta$ and under specular reflection, respectively.

Diffracted beam B+ depicts the first diffraction order, diffracted beam B− depicts the negative first diffraction order. Due to the fact that the first and second grating are fully aligned, the composite grating is symmetrical, i.e. the secondary lines 112 of the first grating 110 coincide with the lines 121 of the second grating 120 as composite lines 112, 121. As a result of the symmetry of the composite grating, the diffraction pattern is also symmetrical: i.e., an intensity I+ of the first order diffracted beam B+ is substantially equal to an intensity I− of the negative first order diffracted beam B−.

$$I+=I-=I_{+0} \qquad \text{eq. (1)},$$

wherein $I_{+0}$ denotes the intensity of first order diffracted beam for the symmetric composite grating.

In FIG. 2c, a cross section of a composite grating 110, 120 is shown which exhibits a non-zero overlay error. The lines 121 of the second grating 120 display an overlay error (misalignment) ∈ relative to the secondary lines 112 of the first grating. As a result, the composite grating as shown in FIG. 2c is asymmetrical: the lines 121 of the second grating 120 are shifted over a distance ∈ in comparison with the secondary lines 112 in the first grating 110.

Due to the asymmetry, the intensity I+ of the first order diffracted beam B+ measured under first oblique incidence angle β is in this case not equal to the intensity I− of the negative first order diffracted beam B−, measured under second oblique angle −β.

For small overlay errors, the change of intensity of a diffracted beam is linearly proportional to the overlay error. The intensity I+ of the first order diffracted beam B+ as a function of overlay error ∈ is in good approximation:

$$I+=I_{+0}+K\times\in \qquad \text{eq. (2)},$$

wherein K is a proportionality factor.

The intensity I− of the negative first order diffracted beam B− is approximated by:

$$I-=I_{+0}-K\times\in \qquad \text{eq. (3)}$$

By taking the difference ΔI=I+−I−, a signal is obtained that scales linearly with the overlay error ∈.

$$\Delta I=2K\times\in \qquad \text{eq. (4)}$$

The proportionality factor K will be discussed in more detail below.

In a further embodiment, overlay metrology may include a use of the first illumination beam IB1 and the second illumination beam IB2 each under substantially normal incidence on the composite grating 110, 120. It will be appreciated by the skilled person that in such an embodiment, the first illumination beam IB1 and the second illumination beam IB2 coincide and are provided as a single illumination beam. The first illumination beam can be used as second illumination beam. Under normal incidence of the illumination beam also, first and negative first order diffraction beams B+, B− will occur. Of these beams B+, B−, the intensity will show the same relationship as described above with reference to FIGS. 2a-2c and equations 1-4. In this embodiment, the intensity difference ΔI of the first and negative first order diffracted beams may be measured by using the first illumination beam and consecutively measuring the intensity of the first and negative first order diffracted beam, respectively.

Figure 3A:
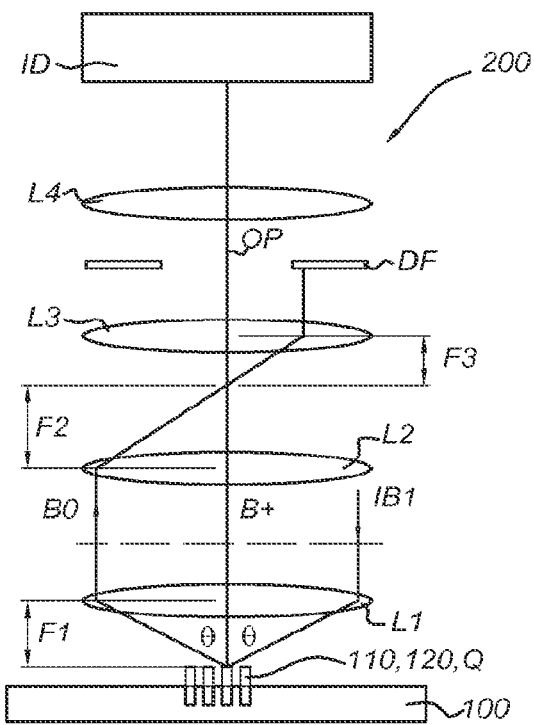
FIGS. 3a, 3b depict a diffraction based overlay error detection system in accordance with an embodiment of the present invention, during a first measurement and a second measurement respectively.

FIG. 3a depicts schematically a diffraction based overlay error detection system (hereafter referred to as detection system) 200 in accordance with an embodiment of the present invention, in a first measurement of the substrate holding the composite grating 110, 120. The detection system may include a support configured to support the substrate in an embodiment of the invention. The support may also be a substrate table of the lithographic apparatus of FIG. 1 in an embodiment of the invention.

The detection system 200 includes a plurality of lenses, in this embodiment, a first, second, third and fourth positive lens L1, L2, L3, L4, an aperture stop DF, and an image detector ID.

Within the detection system 200, an optical axis OP is arranged that extends from a substrate position where a composite grating 110, 120 can be illuminated by the illumination beam IB under oblique incidence angle to a position where an image of the composite grating can be projected on the image detector ID.

For example, the image detector ID may be a CCD camera. The illuminated area is larger than the area of the grating. In other words, the surrounding environment is also illuminated. This is also referred to as "overfill".

Along the optical axis OP, the first, second, third and fourth positive lenses L1, L2, L3, L4 are arranged with their respective centers on the optical axis in such a way that the image of the composite grating 110, 120 can be projected on the image detector ID of the detection system 200.

The first lens L1 is positioned above the substrate position where the composite grating 110, 120 on the substrate 100 can be located. The distance between the first lens and the substrate position is substantially equal to a focal distance F1 of the first lens L1. At some distance from the first lens L1, the second and third lenses L2, L3 are arranged in a pair along the optical axis OP. The fourth lens L4 is arranged as projection lens of the image detector ID. Between the third and the fourth lenses L3, L4, the aperture stop DF is located.

During measurement, the substrate with composite grating 110, 120 is located at the substrate position. The composite grating 110, 120 is in a predetermined position (indicated Q). A first illumination beam IB1 is used in an asymmetric illumination mode under oblique incidence in a first horizontal direction (indicated by arrow D1) along the surface of the substrate. For example, the first illumination beam propagates along a direction that has a component along a first horizontal direction along the surface of the substrate. The first illumination beam IB1 enters the first lens L1, in such way that the first illumination beam IB1 after passing the first lens impinges on the composite grating under an angle that creates a first diffraction order beam B+ under diffraction angle θ. As a result, the first order diffracted beam B+ is now diffracted at the surface of the substrate and a zeroth order diffraction beam B0 is diffracted under specular reflection (in this example under angle 2θ).

Both first order diffracted beam B+ and zeroth order beam B0 pass through the first lens L1. Since the composite grating is at a focal distance F1 of the first lens L1, the first order and zeroth order diffracted beams B+, B0 are directed in parallel after passing the first lens L1.

Next, the first order and zeroth order diffracted beams B+, B0 pass the second lens L2. The first order diffracted beam B+ substantially coincides with the optical axis and passes through the center of the second lens L2. The zeroth order diffracted beam B0 passes the second lens L2 off-axis and after passing is directed through the focal point of the second lens L2.

The third lens L3 is arranged with a focal point F3 coinciding with a focal point F2 of the second lens L2.

The first order diffracted beam B+ coincides with the optical axis of the third lens and passes through the center of the third lens L3 and continues to be on the optical axis. The zeroth order diffracted beam B0 passes the third lens off-axis. Due to the fact that the focal points F2, F3 of the second and third lenses coincide, the zeroth order diffracted beam is substantially parallel to the optical axis after passing the third lens L3.

After the third lens L3 the aperture stop DF is positioned on the optical axis and is arranged to block the zeroth diffraction order. The aperture stop DF allows the first order diffracted beam B+ on the optical axis OP to pass and blocks the zeroth order diffracted beam B0. In this way, the image on the camera is only formed by first diffraction order and not by the zeroth order. This imaging mode is normally called "dark-field" imaging. The aperture stop DF is arranged to have a width that allows to block the zeroth order diffracted beam B0 and allows to let the first order diffracted beam B+ pass.

As a result, an image of the composite grating is formed on the CCD camera using only the first or negative first diffraction order. Suitable image processing and pattern recognition algorithms known to the skilled artisan may then be used to identify the composite grating from the product structures around the composite grating. Application of the aperture stop allows to use an illumination beam with a cross-sectional size larger than the diffraction limit, while the size of the grating may be smaller than indicated by the diffraction limit.

Finally, the first order diffracted beam B+ passes the fourth lens L4 which is arranged for imaging the first order diffracted beam B+ on the image detector ID.

In this manner, an image of the composite grating 110, 120 originated from the first order diffracted beam B+ is projected on the image detector ID. Since the image is only formed by one higher (first) diffraction order, the image will show no modulation of the individual grating lines.

It is noted that the first diffracted order may not necessarily be exactly normal to the surface. The first diffracted order may make any angle with the wafer surface, as long as it is transmitted by the aperture stop (without any other orders passing the aperture stop).

From the image of the composite grating 110, 120 registered on the image detector, the intensity I+ may be determined. The precise location of the image of the grating is determined with pattern recognition algorithms, for example edge detection.

Figure 3B:
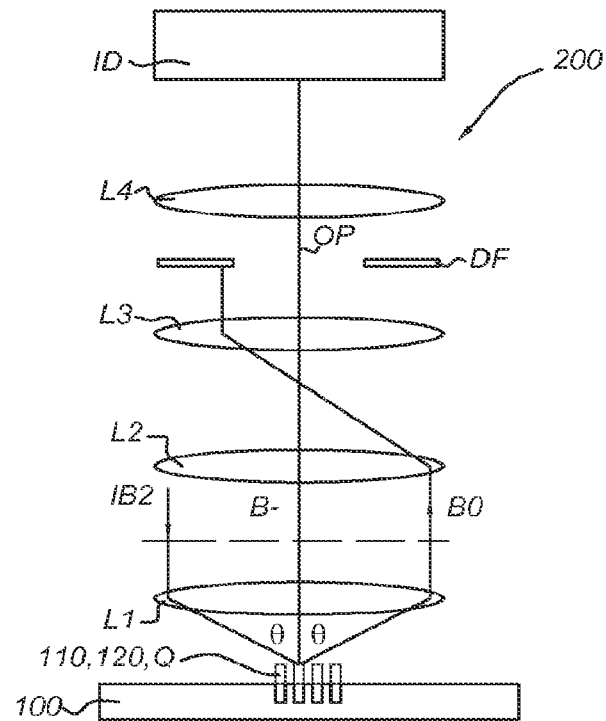

FIG. 3b depicts schematically a diffraction based overlay error detection system in accordance with an embodiment of the present invention, in a second measurement of the substrate holding the composite grating 110, 120.

In FIG. 3b entities with the same reference number as shown in the preceding figures refer to the corresponding entities.

In the second measurement, the composite grating 110, 120 is illuminated asymmetrically by a second illumination beam IB2 in a second horizontal direction (indicated by arrow D2) opposite to the first horizontal direction D1 as used during the first measurement as shown in FIG. 3a. For example, the second illumination beam propagates along a direction that has a component along a first horizontal direction along the surface of the substrate. The composite grating is maintained in the same predetermined position Q as during the first measurement.

Under these conditions, the negative first order diffracted beam B− is now diffracted normal to the surface of the substrate and the zeroth order diffraction beam B0 is diffracted under angle θ. The aperture stop DF is arranged to have a width that allows to block the zeroth order diffracted beam B0 and allows to let the negative first order diffracted beam B− pass.

As a result, during the second measurement an image of the composite grating 110, 120 originated from the negative first order diffraction beam B− is projected on the image detector ID. From the image of the composite grating 110, 120 registered on the image detector ID, the intensity I− may be determined. Again, pattern recognition techniques may be used to identify the region on the CCD where the measurement of the intensity must be carried out.

It is noted that in a different embodiment, the illumination beam has substantially normal incidence. As will be appreciated by the skilled in the art, this embodiment may use a different but functionally equivalent illumination/detection layout in which the function of the aperture stop to allow in a first instance only the first order diffracted beam and in a second instance only the negative first order diffracted beam to pass, would be the same.

Moreover it is noted that oblique incidence is not required but may be preferred since it allows the use of gratings with a smaller pitch.

As described above, the difference of the intensity I+ of the first order diffracted beam B+ and the intensity I− of the negative first order diffracted beam B− is proportional to the overlay error ∈ according to eq. 4. The proportionality factor K is dependent on processing conditions, wavelength of the illumination beam, diffraction angle and polarization. For a given combination of process, wavelength, diffraction angle and polarization, it is desirable to carry out a calibration of the proportionality factor, as will be appreciated by the skilled in the art.

In an embodiment of the invention, the proportionality factor K is calibrated by determining the overlay error ∈ on two biased composite gratings on a substrate. Each biased composite grating has a respective predetermined built-in shift between the first grating 110 and the second grating 120. The two biased gratings are on the substrate in a fixed position relative to each other.

The first biased composite grating has a first built-in shift +d in a shift direction along the grating direction X1. The second biased composite grating has a second built-in shift −d, which is equal to but with opposite sign than the first built-in shift, along the grating direction X1.

In case of an overlay error ∈, the first biased composite grating exhibits a total overlay error ∈+d and the second biased composite grating exhibits a total overlay error ∈−d.

An intensity difference ΔI1 between the first and negative first diffraction orders on the first biased composite grating and an intensity difference ΔI2 between the first and negative first diffraction orders on the second biased composite grating is given by:

$$\Delta I1 = K \times (\in + d) \qquad \text{eq. (5)}$$

for the first biased composite grating and $$\Delta I2 = K \times (\in - d) \qquad \text{eq. (6)}$$

for the second biased composite grating.

Elimination of K results in:

$$\varepsilon = d \frac{\Delta I1 + \Delta I2}{\Delta I1 - \Delta I2} \qquad \text{eq. (7)}$$

In an embodiment, both first and second biased composite gratings can be measured at the same time by the detection system as shown in FIGS. 3a, 3b. In that case the image detector ID registers an image from the first biased composite grating and an image of the second biased composite grating at the same time. By using image processing software the intensity of the image of the first biased composite grating and the intensity of the second biased composite grating can be determined separately. The overlay error $\in$ can be calculated using equations (5)-(7).

Since the first and second illumination beams IB1, IB2 are each under grazing incidence, light that would reflect off surface regions outside of the composite grating(s) (i.e., product area), will not likely reach the image detector ID through the system of first, second, third and fourth lenses L1, L2, L3, L4. In an embodiment of the present invention, the first and/or second illumination beam IB1, IB2 may have a larger cross-section than the composite grating 110, 120 on the substrate without causing interference between light reflected off the surface outside the grating and light diffracted by the composite grating.

A large value of the numerical aperture of the aperture stop DF is preferred since it allows a sharp transition between the composite grating and the surrounding product area in which the composite grating is embedded. Since at the same time, the aperture stop DF is arranged to block the zeroth order diffracted beam B0, the numerical aperture of the aperture stop DF has an upper limit in which a compromise is obtained between sufficient zeroth order diffracted beam suppression and a sufficiently low cross-talk due to reflections from the product area. It is feasible that this approach allows the use of composite gratings of a size of about 10×10 µm2.

It is noted that modeling software may allow to compute a layout of product area and embedded composite grating(s) for which the cross-talk can be minimized further. This approach may allow to design embedded composite gratings with a size of about 4×4 µm2.

In an embodiment, the numerical aperture of the aperture stop DF is about 0.7, while the numerical aperture of the first lens is about 0.95.

Figure 4A:
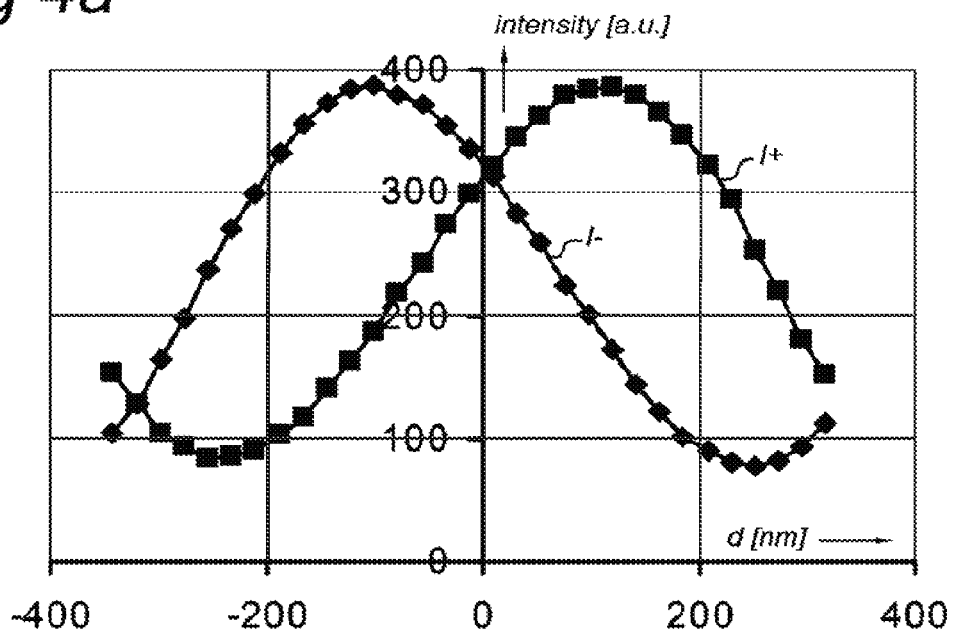
FIG. 4a illustrates exemplary measurements of intensity of a negative first order and first order diffracted beams as function of overlay error.

FIG. 4a illustrates exemplary measurements of intensity of negative first order and first order diffracted beams as function of shift d on a biased grating.

In FIG. 4a, the variation of the intensity I− of the negative first order diffracted beam B− and the intensity I+ of the first order diffracted beam B+ with the shift d are shown for a composite grating with pitch P=660 nm and a wavelength $\lambda$=700 nm of the illumination beam. It is observed that the change of the intensity I+, I− for shifts close to 0 nm is substantially linear.

Figure 4B:
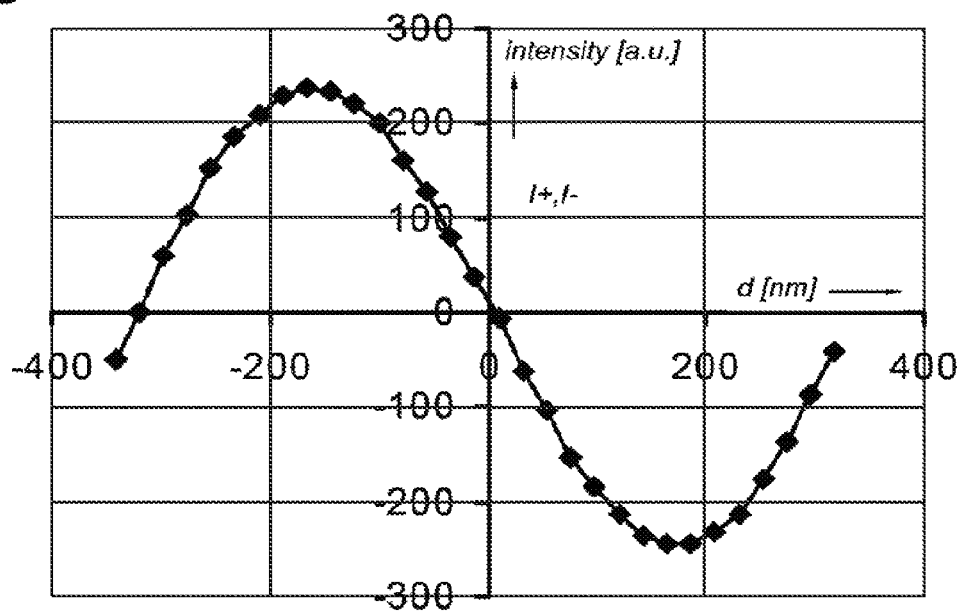
FIG. 4b illustrates a difference of intensity between the negative first order and first order diffracted beams as function of overlay error.

FIG. 4b illustrates the difference of intensity between the negative first order and first order diffracted beams as function of shift d on the biased grating as shown in FIG. 4b. It is observed that the change of the intensity difference $\Delta I$ for shifts close to 0 nm is substantially linear.

Figure 5:
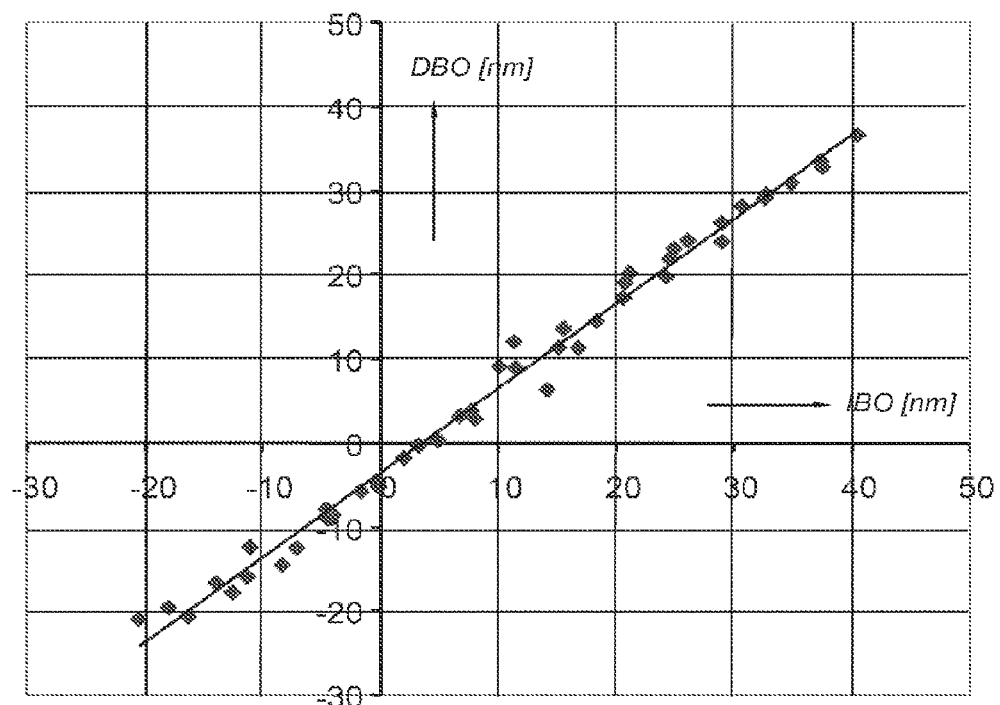
FIG. 5 depicts a correlation between image based overlay error and the diffraction based overlay error as determined according to the present invention.

FIG. 5 depicts a correlation between image based overlay error and the diffraction based overlay error as determined according to the present invention.

For a number of samples, the shift d of the biased composite gratings as measured by diffraction based overlay error metrology is also measured by image based overlay error metrology. In FIG. 5, a correlation is shown of the overlay measured by diffraction (along the vertical axis) and the overlay as measured by an image based method (along the horizontal axis). A linear fit of the data is illustrated by the solid line. Within the error of the methods, the coefficient of the solid line is unity. The correlation coefficient is over 0.99.

It is noted that the illumination beam IB as described above may be a single beam. Alternatively, the illumination beam may have a shape of half an annulus as its cross-section. In that case, the asymmetric illumination in FIG. 3a may be done by one half of the annular beam, while the asymmetric illumination from the opposite direction as shown in FIG. 3b is done by the other half of the annular beam.

The illumination beam IB may be created by a light source such as a monochromatic lamp, or a laser source. A laser source with relatively high intensity may be used in case a short time is available for measurements.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. A method comprising:
   illuminating a composite grating on a surface of a substrate under a normal angle of incidence, the composite grating comprising first and second superimposed gratings with similar pitch;
   measuring, at an image plane, a first intensity of a first diffracted beam from the composite grating;
   measuring a second intensity of a second diffracted beam from the composite grating at the image plane; and
   determining, using an image detector, an overlay error between the first and second gratings based on the first and second measured intensities.

2. The method of claim 1, further comprising:
   determining an intensity difference between the first intensity and the second intensity, the intensity difference being proportional to the overlay error between the first grating and the second grating.

3. The method of claim 1, wherein:
   measuring the first intensity comprises using pattern recognition to detect an image of the composite grating obtained by a positive first order diffracted beam, and
   measuring the second intensity comprises using pattern recognition to detect an image of the composite grating obtained by a negative first order diffracted beam.

4. The method of claim 3, further comprising:
   blocking diffraction orders other than the first diffraction order.

5. The method of claim 1, wherein:
   measuring the first intensity comprises using pattern recognition to detect an image of the composite grating obtained by a zero order diffracted beam, and
   measuring the second intensity comprises using pattern recognition to detect an image of the composite grating obtained by a zero order diffracted beam.

6. The method of claim 1, further comprising:
   illuminating an additional composite grating on the substrate under a normal angle of incidence,
   wherein:
   the additional composite grating is formed by positioning a third grating and a fourth grating on top of the third grating, the third grating and the fourth grating having a substantially identical pitch as the first and the second grating,
   the composite grating is biased with a first shift in a shift direction along a grating direction, and
   the additional composite grating is biased with a second shift in the shift direction along the grating direction, the first shift being equal to but with opposite sign than the second shift.

7. The method of claim 6, further comprising:
   measuring, at the image plane, a third intensity of a third diffracted beam from the additional composite grating; and
   measuring a fourth intensity of a fourth diffracted beam from the additional composite grating at the image plane.

8. A detection system comprising:
   an illumination source configured to direct an illumination beam to diffract from a composite grating on a surface of a substrate under a normal angle of incidence, the composite grating comprising first and second superimposed gratings having a similar pitch;
   an image detector configured to receive, at an image plane, a first diffracted beam and a second diffracted beam from the composite grating and measure their intensities;
   a lens arranged along an optical path between the substrate position and the image detector; and
   an aperture stop,
   wherein the image detector is further configured to determine an overlay error between the first and second gratings based on the measured intensities of the first and second diffracted beams.

9. The detection system of claim 8, wherein:
   the first diffracted beam comprises a positive first order diffracted beam and the second diffracted beam comprises a negative first order diffracted beam, and
   the image detector is configured to use pattern recognition to detect an image of the composite grating using the first order diffracted beam and the negative first order diffracted beam.

10. The detection system of claim 8, wherein the image detector is configured to use pattern recognition to detect an image of the composite grating using only a zero order diffraction beam.

11. The detection system of claim 8, wherein:
    the lens comprises an objective lens adjacent to the surface of the substrate and a projection lens adjacent to the image detector,
    the aperture stop is arranged along the optical path between the objective lens and the projection lens, and
    the objective lens has a first numerical aperture value and the aperture stop has a second numerical aperture value, the second numerical aperture value being smaller than the first numerical aperture value.

12. The detection system of claim 8, wherein the image detector is further configured to determine an intensity difference between the measured intensities of the first diffracted beam and the second diffracted beam, the intensity difference being proportional to the overlay error between the first grating and the second grating.

13. A lithographic apparatus comprising a detection system, comprising:
    an illumination source configured to direct an illumination beam to diffract from a composite grating on a surface of a substrate under a normal angle of incidence, the composite grating comprising first and second superimposed gratings with similar pitch;
    an image detector configured to receive, at an image plane, a first diffracted beam and a second diffracted beam from the composite grating and measure their intensities;
    a lens arranged along an optical path between the substrate position and the image detector; and
    an aperture stop,
    wherein the image detector is further configured to determine an overlay error between the first and second gratings based on the measured intensities of the first and second diffracted beams.

14. The lithographic apparatus according to claim 13, further comprising:
    an illumination system configured to condition a beam of radiation;
    a patterning device support configured to hold a patterning device, the patterning device configured to pattern the beam of radiation to form a patterned beam of radiation;
    a substrate table configured to hold the substrate; and a projection system configured to project the patterned beam of radiation onto the substrate.

15. The lithographic apparatus according to claim 13, wherein:
the first diffracted beam comprises a first order diffracted beam and the second diffracted beam comprises a negative first order diffracted beam, and
the image detector is configured to detect an image of the composite grating using the first order diffracted beam and the negative first order diffracted beam by a pattern recognition method.

16. The lithographic apparatus according to claim 15, wherein the aperture stop is configured to block beams of diffraction order other than the first diffraction order and the negative first diffraction order.

17. The lithographic apparatus according to claim 13, wherein the image detector is configured to detect an image of the composite grating using only a zero order diffraction beam by a pattern recognition method.

18. The lithographic apparatus according to claim 13, wherein:
the lens comprises an objective lens adjacent to the surface of the substrate and a projection lens adjacent to the image detector,
the aperture stop is arranged along the optical path between the objective lens and the projection lens, and
the objective lens has a first numerical aperture value and the aperture stop has a second numerical aperture value, the second numerical aperture value being smaller than the first numerical aperture value.

19. The lithographic apparatus according to claim 13, wherein the image detector is further configured to:
determine an intensity difference between the measured intensities of the first diffracted beam and the second diffracted beam, the intensity difference being proportional to the overlay error between the first grating and the second grating.

* * * * *